United States Patent
Newton et al.

(10) Patent No.: US 8,430,874 B2
(45) Date of Patent: Apr. 30, 2013

(54) ELECTROSURGICAL GENERATOR

(75) Inventors: Michael D. Newton, Wales (GB); Richard J. Curtis, Newport (GB)

(73) Assignee: Gyrus Medical Limited, Cardiff (GB)

( * ) Notice: Subject to any disclaimer, the term of this patent is extended or adjusted under 35 U.S.C. 154(b) by 1006 days.

(21) Appl. No.: 12/149,765

(22) Filed: May 7, 2008

(65) Prior Publication Data

US 2008/0294156 A1 Nov. 27, 2008

Related U.S. Application Data

(60) Provisional application No. 60/929,036, filed on Jun. 8, 2007.

(30) Foreign Application Priority Data

May 24, 2007 (GB) .................................. 0709994.8

(51) Int. Cl.
*A61B 18/18* (2006.01)
(52) U.S. Cl.
USPC .................. 606/38; 606/32; 606/39; 606/40; 607/76; 607/101
(58) Field of Classification Search .................. 606/32, 606/34, 38–40
See application file for complete search history.

(56) References Cited

U.S. PATENT DOCUMENTS

| | | | |
|---|---|---|---|
| 3,885,569 A | 5/1975 | Judson | |
| 6,261,286 B1 | 7/2001 | Goble et al. | |
| 6,270,497 B1 | 8/2001 | Sekino et al. | |
| 6,416,509 B1 | 7/2002 | Goble et al. | |
| 6,514,248 B1 * | 2/2003 | Eggers et al. | 606/41 |
| 6,966,907 B2 | 11/2005 | Goble | |
| 2003/0163124 A1 | 8/2003 | Goble et al. | |
| 2004/0082946 A1 * | 4/2004 | Malis et al. | 606/34 |
| 2004/0260279 A1 | 12/2004 | Goble et al. | |
| 2005/0113820 A1 | 5/2005 | Goble et al. | |

FOREIGN PATENT DOCUMENTS

| | | |
|---|---|---|
| EP | 1 082 944 A | 3/2001 |
| EP | 1 767 162 A | 3/2007 |
| JP | 2000-135222 | 5/2000 |
| JP | 2001-29355 | 2/2001 |
| WO | WO 2004/062516 A | 7/2004 |
| WO | WO 2004/078050 A | 9/2004 |
| WO | WO 2005/117735 A | 12/2005 |
| WO | WO 2006/051252 A1 | 5/2006 |
| WO | WO 2006051252 A1 * | 5/2006 |

OTHER PUBLICATIONS

Search Report issued in U.K. Priority Application GB 0709994.8 (date of search Sep. 18, 2007).

(Continued)

*Primary Examiner* — Laura A Bouchelle
*Assistant Examiner* — Melissa A Snyder
(74) *Attorney, Agent, or Firm* — Nixon & Vanderhye PC

(57) ABSTRACT

An electrosurgical generator includes one or more radio frequency (RF) power sources and an output stage including at least two output lines for connection to an electrosurgical instrument. The generator includes means for measuring a parameter associated with the electrosurgical procedure, such as the impedance measured across two of the output lines. A controller controls the generator such that it delivers a first RF waveform (such as a cutting signal) or a second RF waveform (such as a coagulating signal) to the output lines, and, in a combined mode, both first and second waveforms. The controller automatically adjusts at least one aspect of one or both waveforms in the combined mode, in response to the measured parameter associated with the surgical procedure.

18 Claims, 10 Drawing Sheets

OTHER PUBLICATIONS

International Search Report and Written Opinion of the International Searching Authority issued in corresponding PCT Application No. PCT/GB2008/001727, dated Oct. 29, 2008.

English Translation of Japanese Office Action in corresponding Japanese Application No. 2010-508899, mailed Dec. 18, 2012.

* cited by examiner

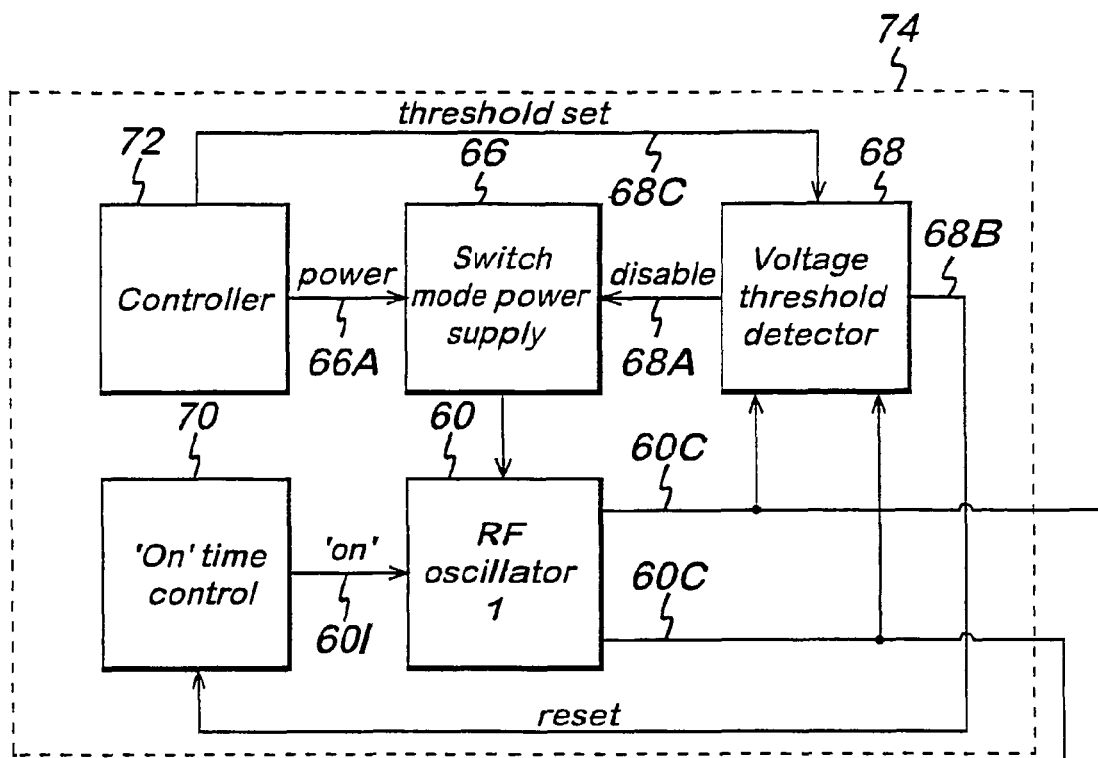
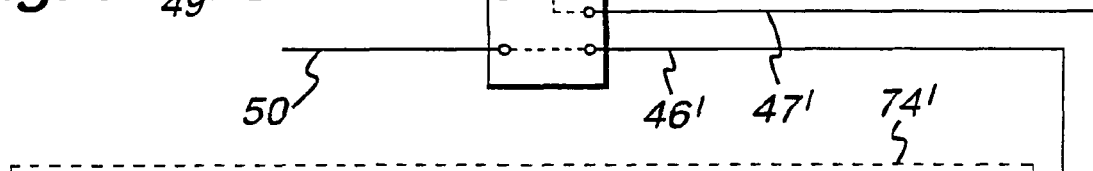
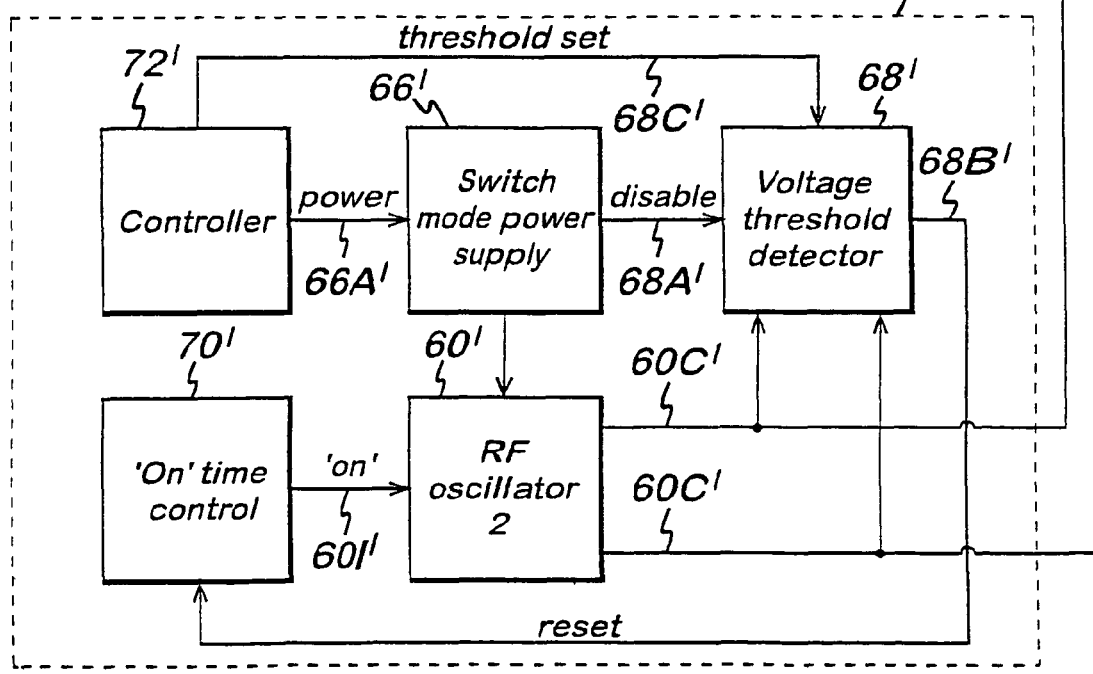
Fig. 9 ured impedance is low, indicating a relatively fluid surgical environment associated with bleeding tissue, the electrosurgical system could increase the coagulating effectiveness of the electrosurgical instrument. Conversely, when the measured impedance is higher, indicating a relatively dry surgical environment, the electrosurgical system could increase the cutting effectiveness of the electrosurgical instrument, in order to maximise the speed and efficiency of the cutting process. Where there are more than two output lines, the impedance can be measured across any two pairs of output lines, even conceivably across different pairs of output lines at different times during the operation of the generator.

ELECTROSURGICAL GENERATOR

CROSS-REFERENCE TO RELATED APPLICATION

This application claims priority to United Kingdom Application No. 0709994.8, filed 24 May 2007, and claims benefit of U.S. Provisional Application No. 60/929,036, filed 8 Jun. 2007, the entire contents of each of which are hereby incorporated by reference.

FIELD OF THE INVENTION

This invention relates to an electrosurgical generator for use with a bipolar electrosurgical instrument for use in the treatment of tissue.

BACKGROUND OF THE INVENTION

U.S. Pat. Nos. 6,416,509 and 6,966,907 describe different ways in which electrosurgical generators can deliver a blend of cutting and coagulating signals in order to perform the simultaneous cutting and hemostasis of tissue. In a more recent U.S. patent application Ser. No. 10/858,406, published as US 2004/0260279, a user of the electrosurgical generator is able to select manually between various preset settings for the ratio between cutting and coagulation delivered by the generator.

The disclosure of the above prior patents and patent application is incorporated herein by reference. The present invention seeks to provide a further improvement to these types of electrosurgical generators.

SUMMARY OF THE INVENTION

According to the present invention, an electrosurgical generator for generating radio frequency (RF) power for supply to an electrosurgical instrument is provided, the generator comprising
(i) one or more sources of RF output power,
(ii) an output stage including at least two output lines adapted to be connected to the electrosurgical instrument,
(ii) an output stage including at least two output lines adapted to be connected to the electrosurgical instrument,
(iii) means for measuring a parameter associated with the electrosurgical procedure, and
(iv) a controller operable to control the generator system such that it is capable of delivering a first RF waveform to the output lines or a second RF waveform to the output lines, and, in a combined mode, to deliver both first and second RF waveforms, the arrangement being such that, in the combined mode, the controller automatically adjusts at least one aspect of one or both of the first RF waveform and the second RF waveform in response to the measured parameter associated with the surgical procedure.

In this way, as opposed to waiting for the surgeon using the electrosurgical generator to adjust manually the performance of the electrosurgical instrument, the generator reacts to the parameter being measured in order to adjust automatically the electrosurgical signals being delivered to the tissue. In this way, the electrosurgical generator adjusts itself dynamically in response to different operating conditions, selecting different electrosurgical signals as required for effective operation. Conceivably a plurality of different parameters could be measured and used to adjust the electrosurgical generator.

Conveniently, the measured parameter is the impedance measured across any two of the output lines. Thus, when the measured impedance is low, indicating a relatively fluid surgical environment associated with bleeding tissue, the electrosurgical system could increase the coagulating effectiveness of the electrosurgical instrument. Conversely, when the measured impedance is higher, indicating a relatively dry surgical environment, the electrosurgical system could increase the cutting effectiveness of the electrosurgical instrument, in order to maximise the speed and efficiency of the cutting process. Where there are more than two output lines, the impedance can be measured across any two pairs of output lines, even conceivably across different pairs of output lines at different times during the operation of the generator.

In one convenient arrangement, the electrosurgical generator includes first and second sources of radio frequency (RF) power, the first source being connected to deliver the first RF waveform, and the second source being connected to deliver the second RF waveform. In this way, each source can be optimized for its particular purpose, in terms of frequency, power, etc. With first and second sources, in the combined mode, the controller is conveniently adapted to supply RF waveforms from the first and second sources continuously. In response to the measured parameter such as impedance, the controller could conceivably increase or decrease the power of either the first or second sources, or alternatively change the frequency of operation of either source, to affect a change to the cutting or coagulating performance of the electrosurgical instrument.

Alternatively, in the combined mode, the controller is adapted to supply RF waveforms from at least one of the first and second sources discontinuously. Conveniently, the controller is adapted to switch in and out the connection of the first and/or second sources to deliver the first RF waveform and the second waveform discontinuously.

As described above, the generator can supply a number of different signals, including but not limited to the following;
i) simultaneous continuous signals from the first and second sources;
ii) a continuous signal from the first source, with an intermittent signal from the second source;
iii) a continuous signal from the second source, with an intermittent signal from the first source;
iv) alternate signals from the first and second sources, in a continuously alternating fashion; and
v) intermittent signals from both the first and second sources, with gaps therebetween.

In another alternative arrangement, the generator includes a single source of radio frequency (RF) power, the controller being adapted in the combined mode to alternate between delivering the first RF waveform and the second RF waveform to the output lines as an alternating signal.

Conveniently, the aspect of the first and second waveforms that is varied in response to the measured parameter is selected from the power, the voltage, the current or even the frequency of the first RF waveform or the second RF waveform. Alternatively, the measured parameter could include the phase of the first and second RF waveforms.

In one convenient arrangement, the first RF waveform is a cutting RF waveform designed to produce the electrosurgical cutting of tissue, and the second RF waveform is a coagulating RF waveform designed to produce the electrosurgical coagulation of tissue. Thus, when the measured impedance is low, indicating a relatively fluid surgical environment associated with bleeding tissue, the electrosurgical system could increase the proportion of the coagulating signal applied to the tissue. Conversely, when the measured impedance is higher, indicating a relatively dry surgical environment, the electrosurgical system could increase the proportion of the cutting signal applied to the tissue, in order to maximise the speed and efficiency of the cutting process.

In a preferred arrangement, the controller is operable to limit the radio frequency peak output voltage developed across the output connections to at least a first predetermined threshold value for cutting to produce the first cutting RF waveform, and second predetermined threshold value for coagulation to produce the second coagulating RF waveform and, in the combined mode of the generator, to alternate constantly between said first and second threshold values.

Whether one or two sources of RF power are employed, where the cutting and coagulating waveforms are supplied intermittently, the "first duty cycle" is that part of the overall signal during which the first cutting RF waveform is supplied to the output lines, and the "second duty cycle" is that part of the overall signal during which the second coagulating RF waveform is supplied to the output lines. Most conveniently, the aspect that is adjusted in response to the measured parameter is one or both of the first and second duty cycles. In this way, the proportion of the overall signal that is dedicated to delivering the coagulating signal can be increased when the measured parameter indicates that more coagulating effectiveness is required. Conversely, the proportion of the overall signal that is dedicated to delivering the cutting signal can be increased when the measured parameter indicates that less coagulating effectiveness is required. It should be pointed out that it is not necessary for the first and second duty cycles to constitute 100% (i.e. there may deliberately be gaps left between the cut and coag parts of the waveform).

Whereas the electrosurgical generator as described above can be utilized with bipolar electrosurgical instruments having two electrodes (and hence the generator has only two output lines), the generator according to the invention can also be utilized with electrosurgical instruments having more than two electrodes, such as those described in our U.S. Pat. No. 6,696,907. Accordingly, the generator includes at least three output lines, and also including a selection arrangement for varying the coupling between the one or more sources and the three output lines such that, in the combined mode, that part of the combined signal that is the first RF waveform is delivered between a first pair of the output lines, and that part of the combined signal that is the second RF waveform is delivered between a second pair of the output lines.

Where the first RF waveform is a cutting waveform, and the second RF waveform is a coagulating waveform, the coagulating signal is delivered between two electrodes optimised for the coagulation of tissue, while the cutting signal is delivered to a different electrode optimised for the cutting of tissue. This optimisation is described more fully in U.S. Pat. No. 6,696,907, as well as in the following description.

However, the first and second RF waveforms do not necessarily have to be cutting and coagulating waveforms respectively. In one conceivable arrangement both the first and second RF waveforms can be cutting RF waveforms, designed to produce the electrosurgical cutting of tissue. As the first and second waveforms are supplied to different sets of electrodes, the width of the RF cut produced by the electrosurgical instrument can be varied by increasing or decreasing the proportion of the first and second RF signals supplied to the instrument. Alternatively, both the first and second RF waveforms can be coagulating RF waveforms, designed to produce the electrosurgical coagulation of tissue. In this arrangement, the width of the RF coagulation lesion produced by the electrosurgical instrument can be varied by increasing or decreasing the proportion of the first and second RF signals supplied to the instrument.

The invention will be described below in more detail, by way of example only, with reference to the accompanying drawings.

BRIEF DESCRIPTION OF THE DRAWINGS

In the drawings:

FIG. 9 is a block diagram of an alternative embodiment of generator system in accordance with the present invention;

DETAILED DESCRIPTION OF PREFERRED EMBODIMENTS OF THE INVENTION

Figure 1:
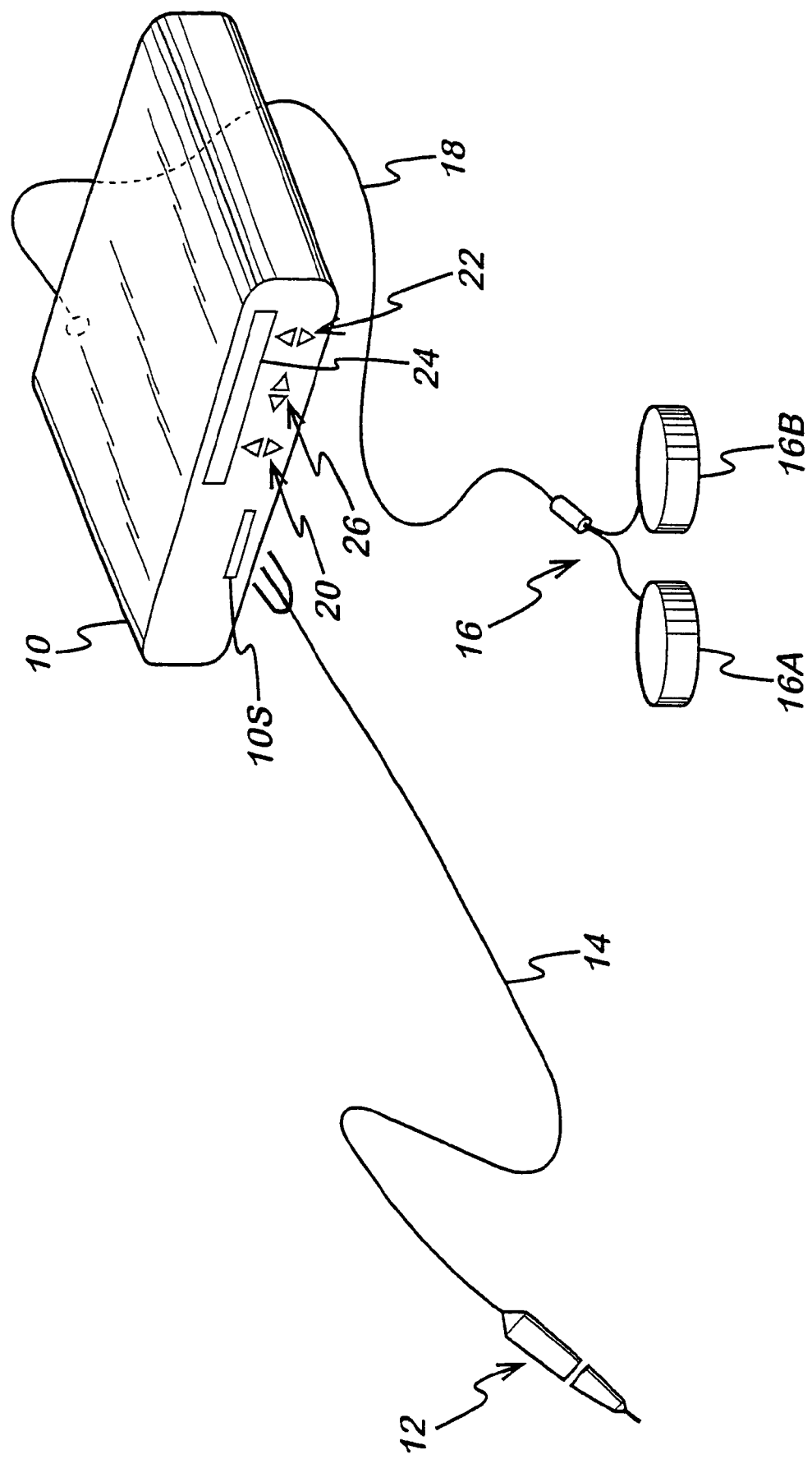
FIG. 1 is a schematic view of an electrosurgical system including an electrosurgical generator according to the invention.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two pedals 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
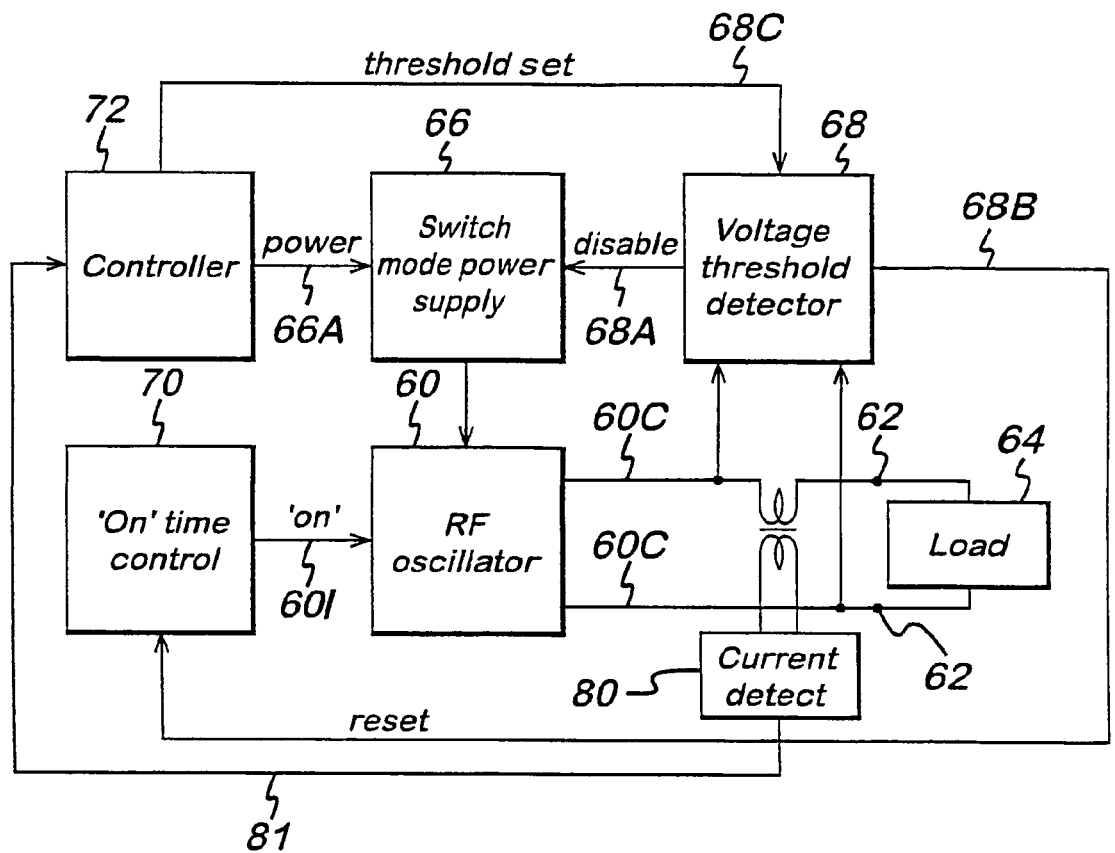
FIG. 2 is a block diagram of the generator of FIG. 1.

Referring to FIG. 2, the generator comprises a radio frequency (RF) power oscillator 60 having a pair of output lines 60C for coupling to the instrument 12. The instrument 12 is shown in FIG. 2 in the form of an electrical load 64. Power is supplied to the oscillator 60 by a switched mode power supply 66. In the preferred embodiment, the RF oscillator 60 operates at about 400 kHz, with any frequency from 300 kHz upwards into the HF range being feasible. The switched mode power supply typically operates at a frequency in the range of from 20 to 50 kHz. Coupled across the output lines 60C is a voltage threshold detector 68 having a first output 68A coupled to the switched mode power supply 16 and a second output 68B coupled to an "on" time control circuit 70. A microprocessor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits. Also coupled in one of the output lines 60C is a current detection circuit 80 which feeds a signal $V_I$ representative of the load current via line 81 to the controller 72.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). An output voltage threshold is set independently on the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved. When a combined mode output is required, the voltage output set via input 68C is constantly alternated between the value for desiccation or coagulation and the value for cutting or vaporisation, to form a blended signal.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each oscillation cycle. The power delivered to the load 64 depends partly on the supply voltage applied to the RF oscillator 60 from the switched mode power supply 66 and partly on the load impedance 64. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

Figure 3:
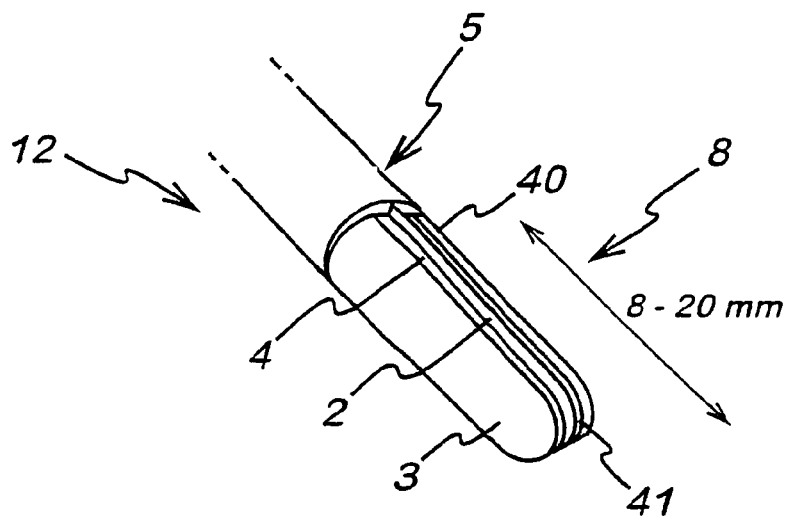
FIG. 3 is a schematic perspective view of an electrosurgical instrument used as a part of the system of FIG. 1.

FIG. 3 shows one possible design for the electrosurgical instrument 12. The instrument 12 comprises an instrument shaft 5 at the distal end of which is an electrode assembly shown generally at 8. The electrode assembly 8 comprises a central cutting electrode 2 disposed between two larger coagulation electrodes 3 and 40. Insulating layer 4 separates the cutting electrode 2 from the first coagulating electrode 3, while an insulating layer 41 separates the cutting electrode 2 from the second coagulation electrode 40. The cutting electrode 2 protrudes slightly beyond the two coagulating electrodes.

When the user intends the instrument to cut tissue, the generator applies a cutting RF signal between the cutting electrode 2 and one or both of the two coagulating electrodes 3 and 40. Conversely, when the user intends the instrument to coagulate tissue, the generator applies a coagulating RF signal between the two coagulating electrodes 3 and 40. The application of the blended RF signal will be described with reference to the switching circuit shown in FIG. 4.

Figure 4:
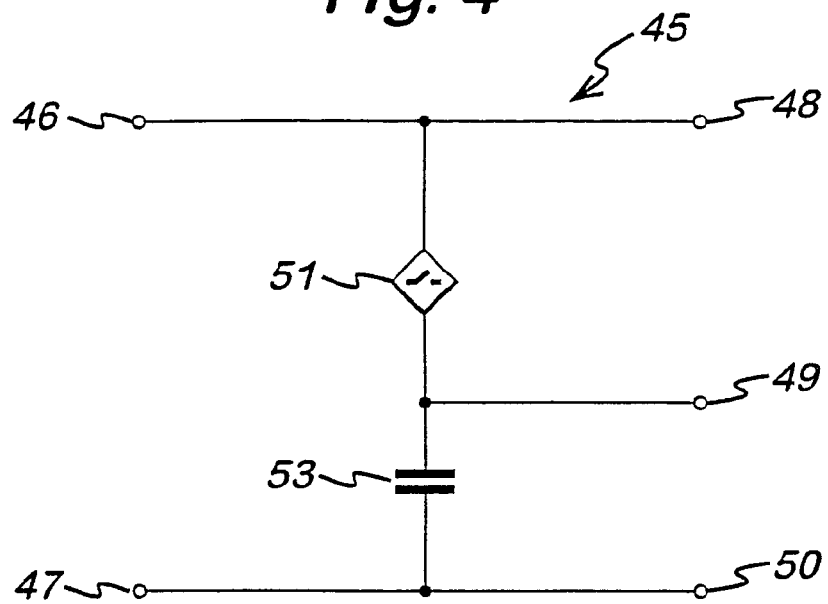
FIG. 4 is a schematic diagram of a switching circuit used in the generator of FIG. 2.

FIG. 4 shows a switching circuit shown generally at 45 and comprising input connections 46 and 47 connected respectively to the two output lines 60C of the generator 10. Switching circuit 45 has three output connections 48, 49 and 50. Output connection 48 is connected to the cutting electrode 2 in the device of FIG. 3. Output connections 49 and 50 are respectively connected to the coagulating electrodes 3 and 40 in the device of FIG. 3. An electronic switch device 51 is connected between output connections 48 and 49. The switch 51 is capable of rapidly making and breaking the connection between the output lines 48 and 49. A capacitor 53 is connected between the output connections 49 and 50, the capacitor typically having a value of between 1 and 10 nF.

When the user actuates the pedals 16A or 16B to operate the instrument 12 in the blended mode, the generator supplies alternating bursts of the RF cutting and coagulating signals to the input connections 46 and 47. The switch device 51 operates synchronised with the alternating RF signals such that when that part of the signal containing the cutting signal is received, the switch device is open such that there is open circuit between the output connections 48 and 49. Thus the cutting RF signal is supplied between cutting electrode 2 and coagulating electrode 40, via output connections 48 and 50 respectively. Conversely, when that part of the signal containing the coagulating voltage is received across the input connections 46 and 47, the switching device 51 is closed such that output connections 48 and 49 are in electrical communication one with the other. Thus, during the coagulation part of the blended signal, the signal is supplied between the two coagulation electrodes 3 and 40, via output connections 49 and 50, with the capacitor 53 providing a potential difference therebetween.

Figure 5A:
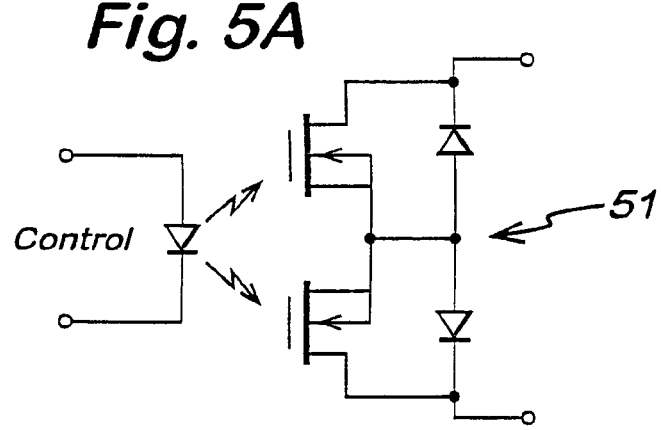
FIGS. 5A and 5B are circuit diagrams of two electronic switching devices for the switching circuit of FIG. 4.

Switching device 51 may comprise an AC opto-relay such as the optically coupled dual FET arrangement shown in FIG. 5A. Another switching device providing isolation between control circuitry and the output lines is the combination of an AC bridge and a single MOSFET switch controlled via an isolating driver, a shown in FIG. 5B.

The above description is based upon the generator 10 controlling the blended mode signal, and the switching device 51 opening and closing synchronously therewith. However, this does not have to be the case and the switching device can control the generator in order to determine the changeover between the cutting and coagulation RF signals.

Consider the switching circuit 45 as shown in FIG. 4. When the switching device 51 is in its open condition, the cutting signal is supplied across output connections 48 and 50. When the switching device 51 closes, the cutting signal is initially supplied between the output connections 49 and 50, separated by the capacitor 53. This causes the current delivered by the generator to rise rapidly such that the current limiting circuitry within the generator operates to reduce the power being delivered, such that the signal rapidly converts to an RF signal typical for coagulation. The effect of the current limiting circuitry within the generator is that the closing of the switching device 51 causes the signal being delivered to be transformed, almost instantaneously, from a cutting signal to a coagulating signal. Conversely, when the switching device 51 opens again, the generator ceases to be current limited, and the signal once again rapidly reverts to being a cutting RF signal. In this way, the opening and closing of the switching device 51 toggles the generator between its cutting and coagulating modes, producing the blended signal which is supplied to the electrodes of the instrument 12.

Figure 6:
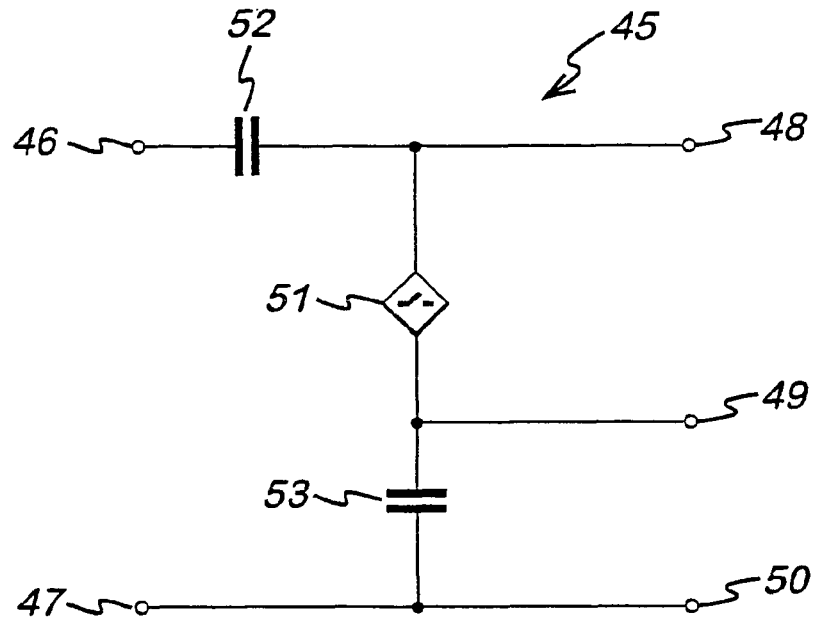
FIG. 6 is a schematic diagram of an alternative embodiment of switching circuit which can be used in the generator of FIG. 2.
Figure 7:
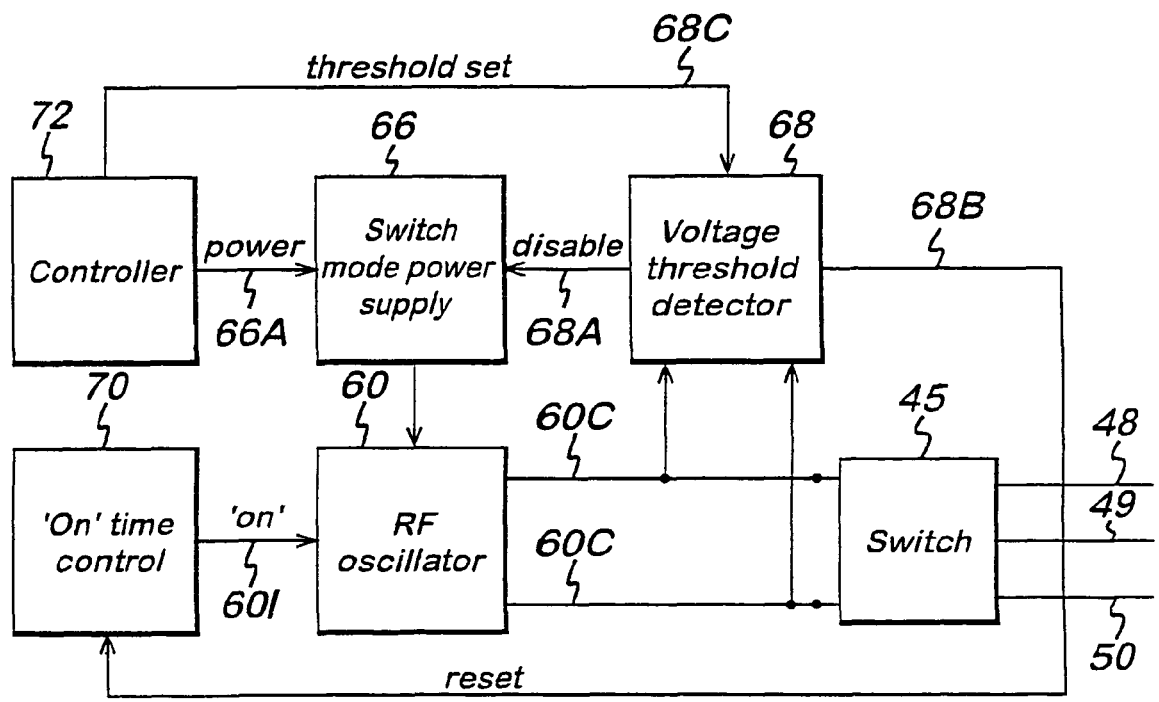
FIG. 7 is a block diagram of a generator in accordance with FIG. 2, incorporating a switching circuit in accordance with FIG. 4.

FIG. 6 shows an alternative embodiment of switching circuit, which can be employed if the generator 10 is not a current limited generator, or if it is desired not to use the current limiting features of the generator. The switching circuit of FIG. 6 is almost identical to that of FIG. 4, the main difference being the addition of an additional capacitor 52 in series with the input connection 46. The capacitor 52 typically has a value one half of that of capacitor 53, such that the voltage delivered across output connections 49 and 50 is divided down to a level typically used for coagulation without reducing the power output of the generator 10. In this way a cutting RF signal is delivered between output connections 48 and 50 when the switching device 51 is open, and a coagulating RF signal is delivered between output connections 49 and 50 when the switching device is closed.

Figure 5B:
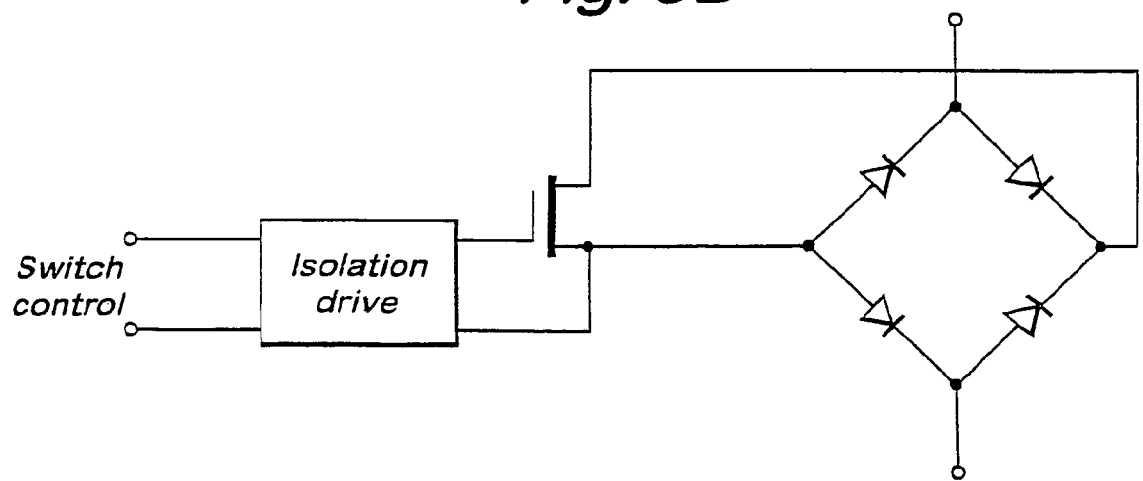

As in the arrangement described above in FIG. 4, the switching device 51 of the alternative switching circuit of FIG. 6 may be as shown in FIG. 5A or FIG. 5B, the driving signal being obtained from a source associated with the switching device itself or from control circuitry within the generator which controls other generator functions.

FIG. 9 shows an alternative generator system in which two RF source circuits 74 and 74' are employed. Source circuit 74 comprises RF oscillator 60 and its associated power supply and control elements. The source circuit is as described with reference to FIG. 2, and like elements are given the same reference numerals as in FIG. 2. The second source circuit 74' comprises a second RF oscillator 60', along with a second controller 72', power supply 66', voltage threshold detector 68' and on time control circuit 70'. FIG. 9 shows the source circuit 74' as having its own dedicated version of each of these units, although it is feasible that certain of them (such as the power supply 66' and controller 72') could be shared with the source circuit 74. The voltage threshold detector 68 is set such that the output connections 60C from source circuit 74 provide an output power signal having a cutting RF waveform, while the voltage threshold detector 68' is set such that the output connections 60C' from source circuit 74' provide an output power signal having a coagulating RF waveform. The second oscillator 60' operates at a different frequency from that of oscillator 60.

A common output stage 73 is provided for both source circuits 74 and 74'. Output connections 60C from source circuit 74 are connected to input connections 46 and 47 of the output stage 73, while output connections 60C' from source circuit 74' are connected to input connections 46' and 47' of the output stage respectively. Within the output stage 73, input connections 47 and 47' are both connected to output connection 49, while input connection 46 is connected to output connection 48, and input connection 46' to output connection 50. The result of this arrangement is that the cutting RF signal from source circuit 74 is delivered between output connections 48 and 49 and hence to one pair of electrodes on the electrosurgical instrument 12. Simultaneously, the coagulating RF signal from source circuit 74' is delivered between output connections 49 and 50 and hence to a different pair of electrodes of the instrument 12. Thus the electrosurgical instrument 12 is able simultaneously to cut and coagulate tissue by virtue of the two different frequency signals. As before, the advantage is that the cutting signal and the coagulating signal, whether they be applied simultaneously or in an alternating blended signal, are delivered to different pairs of electrodes of the electrosurgical instrument. The design of these electrodes can therefore be optimised, depending on whether they are intended to cut or coagulate tissue.

Figure 10:
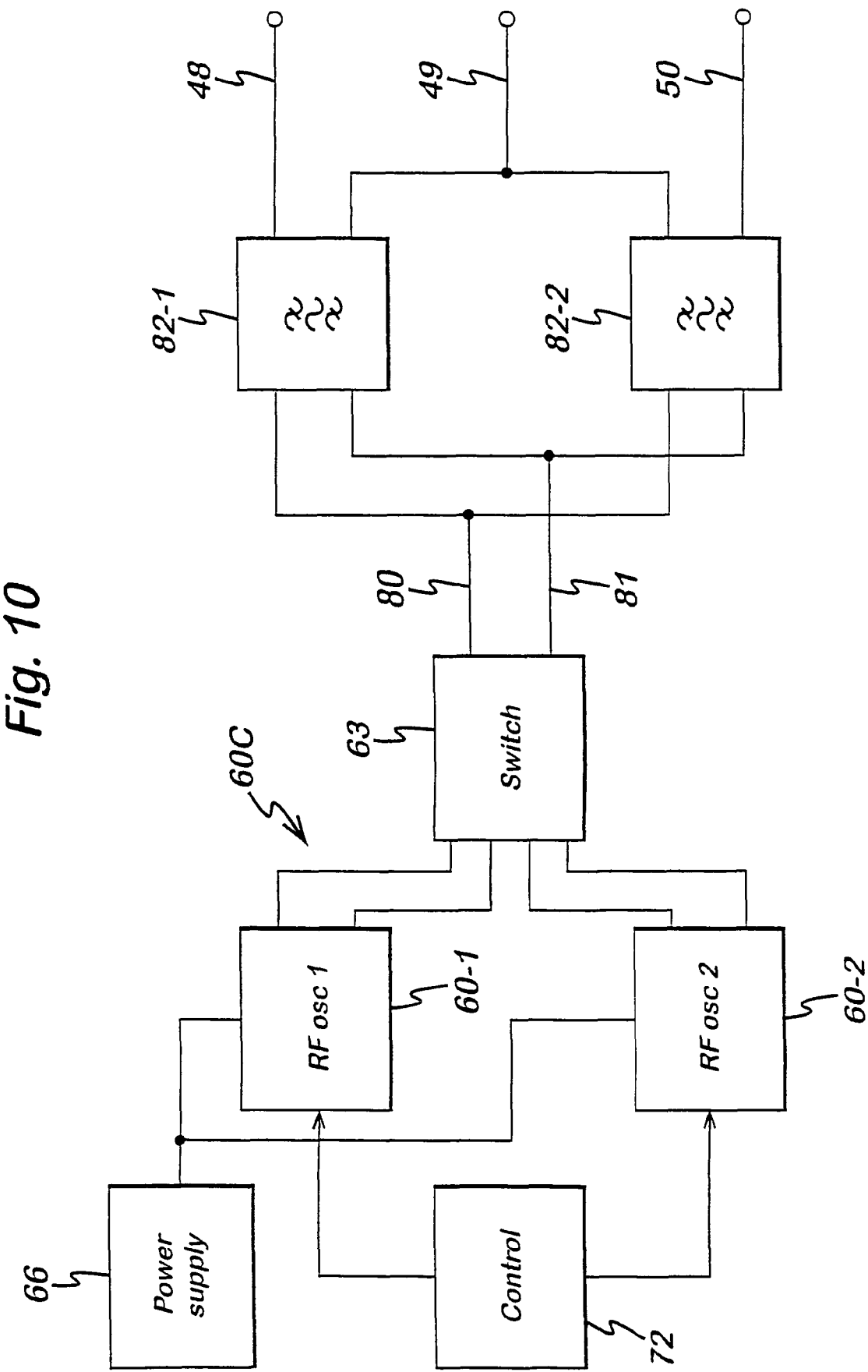
FIG. 10 is a block diagram of a further alternative generator system in accordance with the invention.

Referring to FIG. 10, in an further alternative generator and instrument combination, two RF power oscillators 60-1 and 60-2 are powered from a common power supply 66 and are controlled by a common controller 72 to produce on respective output lines 60C an RF power signal suitable for cutting and an RF power signal suitable for coagulation. These signals may be fed to a switching circuit 63 for selecting the power signal from one oscillator 60-1 or the other oscillator 60-2 according to inputs from, for instance, foot switches, the selected power signal being transmitted on output connections 80, 81. In a blended mode, the switch is operated repeatedly at a predetermined rate to produce a blended output power signal across connections 80, 81. The power oscillators 60-1, 60-2 are operated at different frequencies, and the respective cut and coagulation signals are fed to the required electrodes by feeding the power signal on output connections 80, 81 to tuned circuits 82-1 and 82-2 tuned to the different frequencies. The outputs of the tuned circuits are coupled via electrode lines 48, 49 and 50 to the respective electrodes of the electrosurgical instrument. In this way, the cutting signal from oscillator 60-1 is fed to a cutting electrode 48 and a common electrode 49, whereas the coagulation signal from oscillator 60-2 is fed to a coagulation electrode 50 and the common electrode 49.

In the embodiment shown in FIG. 10, the connection between the electrosurgical generator and the electrosurgical instrument is typically provided by output connections 80 and 81, but the apportionment of circuit blocks between the generator and the instrument may be varied.

Figure 11A:
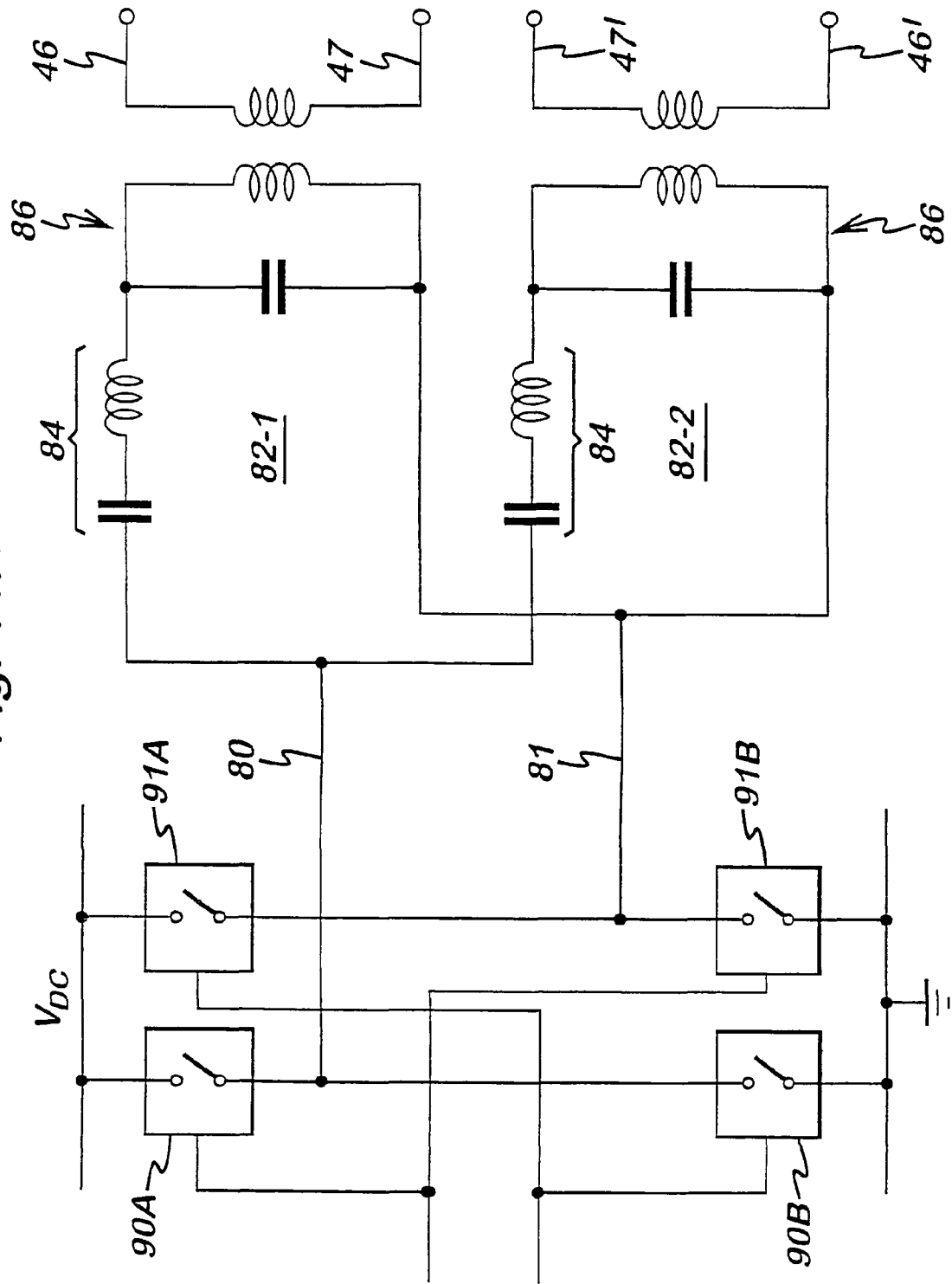
FIGS. 11A and 11B are yet further alternative systems for feeding cut and coagulation outputs automatically to different respective electrode pairs.
Figure 11B:
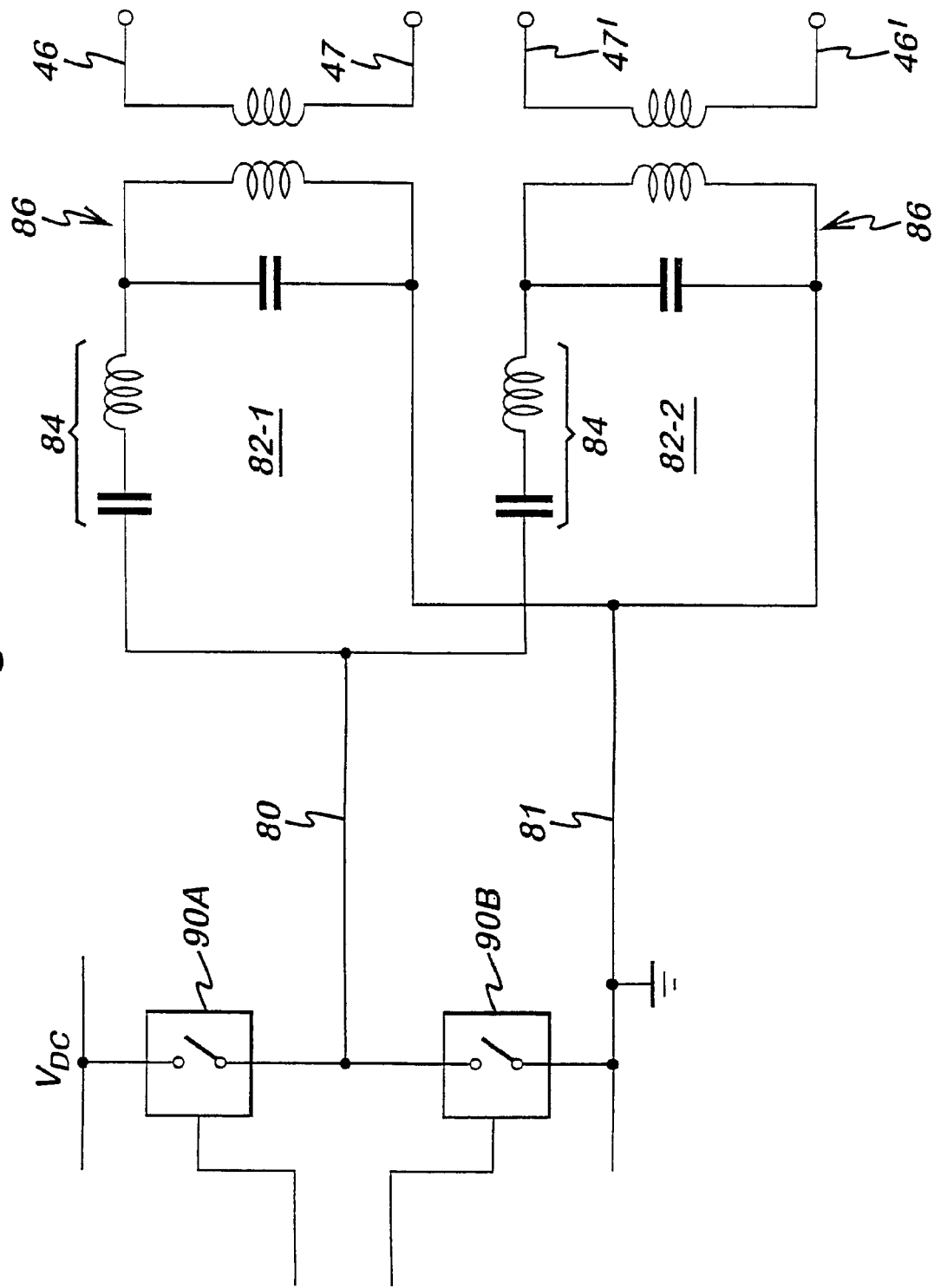

Further embodiments are shown in FIGS. 11A and 11B. Like the embodiment of FIG. 9, these embodiments dispense with the need for a signal routing switch or switching circuit.

Referring to FIG. 11, there are provided two tuned circuits 82-1 and 82-2 (as in FIG. 10), tuned to different frequencies. Each has a series-resonant inductor-capacitor pair 84 and a parallel-resonant inductor-capacitor pair 86, the latter being transformer coupled to output connections 46 and 47 on the one hand and 46' and 47' on the other hand. As in the embodiment of FIG. 10, each tuned circuit has two inputs, one of which is connected to a generator output connection 80 and the other of which is connected to a generator output connection 81. In this embodiment, the generator has an output stage comprising RF switches arranged in two oppositely acting push-pull pairs 90A, 90B and 91A, 91B. Typically these switches comprise power MOSFETS. Each switch 90A, 90B, 91A, 91B is connected to driver inputs 92, 93, as shown, which receive an RF drive signal which, for producing on the output connections 80, 81 an output having a cut waveform is at one RF frequency, and for producing a coagulation output on the output connections 80, 81, has a different RF frequency, these frequencies being, respectively, the resonant frequency of, the resonant combinations 84, 86 of the first tuned circuit 82-1 and, the resonant frequency of the corresponding resonant combinations of the other tuned circuit 82-2. As described above, the RF switches 90A, 90B, 91A and 91B of the generator output stage may be driven according to, for instance, a footswitch control to produce a cut output or a coagulation output. Again, additionally, a blended output may be produced in which the RF frequency alternates constantly between the two resonant frequencies of the tuned output circuits.

The embodiment of FIG. 11B is a modification of that of FIG. 11A, in which the generator output stage has a single push-pull pair of RF switches 90A, 90B and in which the tuned circuits each have one input connected to the junction between the switches 90A, 90B and the other input connected to ground.

Figure 12A:
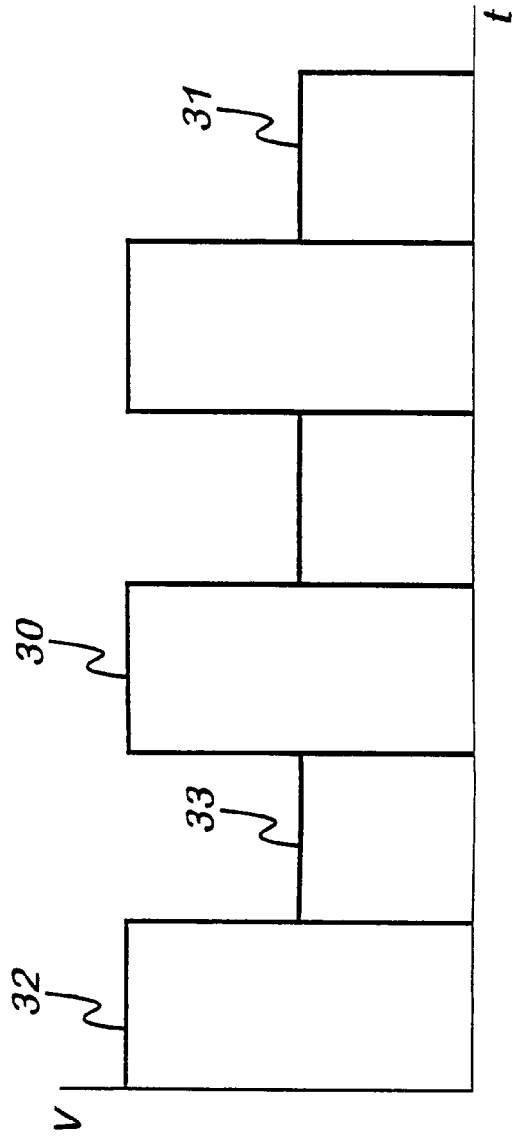
FIGS. 12A and 12B are diagrams showing control envelopes for different blend signals capable of being produced by a generator in accordance with the invention.

FIG. 12A shows a voltage control envelope for a first blended signal which comprises a constantly alternating combination of a cut signal envelope 30 and a coag signal envelope 31. The envelope of the cut signal 30 defines a first voltage threshold 32, which limits the voltage of the cut signal, while the envelope 31 of the coag signal defines a (lower) voltage threshold 33 which limits the voltage of the coag signal. The cut signal is supplied with a 50% duty cycle, and the coag signal is also supplied with a 50% duty cycle, representing the remainder of the composite, blended signal. This output signal produces a tissue effect which simultaneously cuts and coagulates tissue.

Figure 12B:
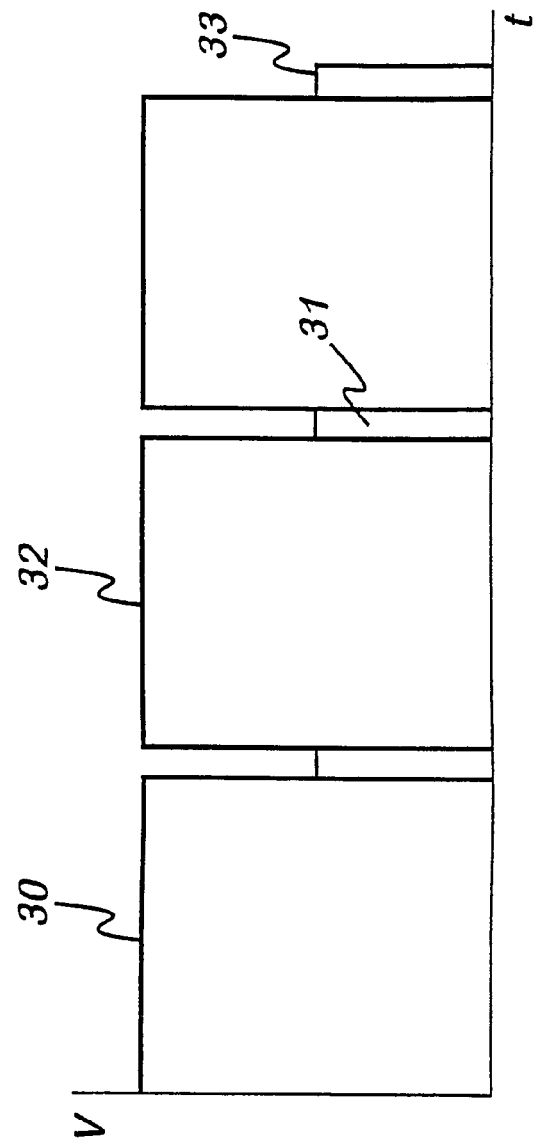

FIG. 12B shows the voltage control envelope of an alternative blended output signal, again alternating constantly between a cut signal envelope 30 and a coag signal envelope 31, each defining voltage thresholds 32 and 33 respectively. However, in this case, the composite output signal, the cut signal is supplied with a 90% duty cycle, and the coag signal is supplied with only a 10% duty cycle. This output signal will cut tissue more effectively than the signal of FIG. 12A, but will have less of a coagulative effect on the tissue being treated. As mentioned previously, the duty cycles for the cut and coag signals do not necessarily total 100%, and there may be deliberate gaps left between the activation of the cut and coag parts of the overall signal.

The controller 72 measures the impedance across output lines 60C (in the two output line embodiments such as FIG. 2), or across any two of the three output lines 48, 49 & 50 (in the three output line embodiments such as FIGS. 4, 5, 7, 9, 10 & 11). The controller 72 uses the measured impedance to alter the proportion of the cut and coag signals being supplied to the output lines. For example, if the measured impedance is below a threshold value (indicating a relatively wet surgical field indicative of the presence of blood or other fluids) the controller can supply the waveform of FIG. 12A, with a 50% coagulative content to the signal. Conversely, if the measured impedance is above a threshold value (indicating a relatively dry surgical field), the controller can supply the waveform of FIG. 12B, with a 90% cut content to the signal. This will allow for the most efficient and beneficial speed of cutting while the field remains relatively dry, but with an increased coag content once bleeding is encountered.

The skilled man will appreciate that the two arrangements of FIGS. 12A and 12B are not the only possibilities for the variation in the effectiveness of the cut and coag signals. Indeed, either a broad range of preset settings, or even a continuous adjustment of the cut and coag signals could be used. The effect is such that a surgeon, on encountering a change in the surgical conditions (such as an increase in the amount of bleeding), does not need to adjust the generator settings manually. The generator senses the change in surgical conditions by measuring the load impedance or other surgical parameter, and adjust the output automatically.

Figure 8A:
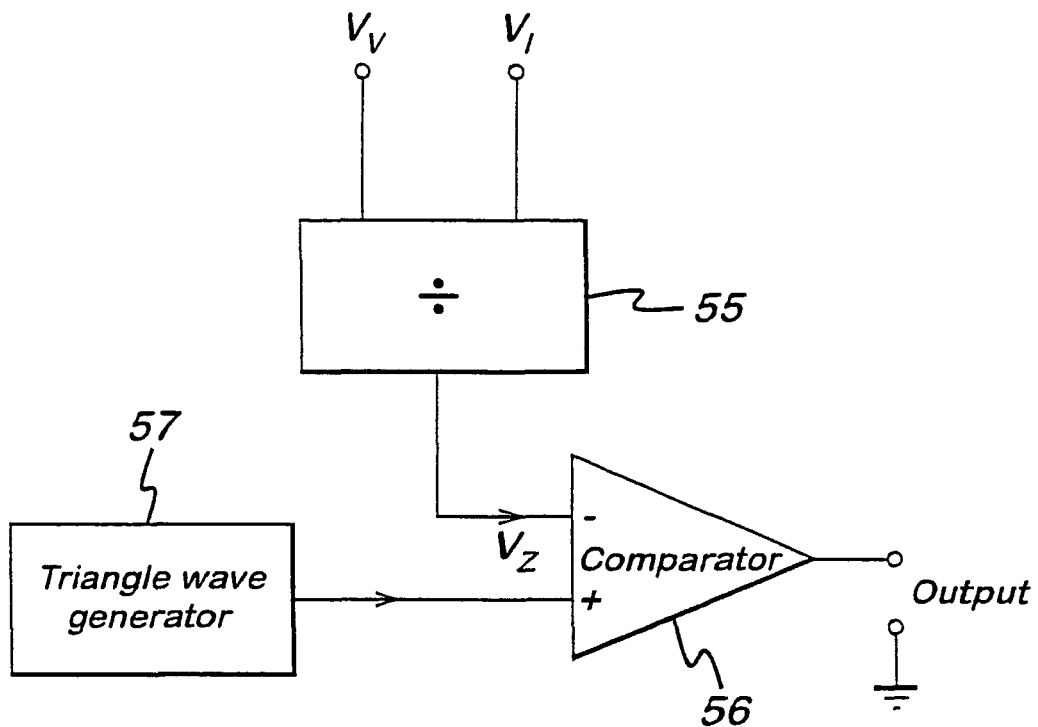
FIGS. 8A and 8B are diagrams illustrating a technique for automatically adjusting a blend switching ratio in response to a measured parameter, FIG. 8A being a circuit diagram of a ratio adjusting device and FIG. 8B being a waveform diagram illustrating the operation of the device of FIG. 8A.
Figure 8B:
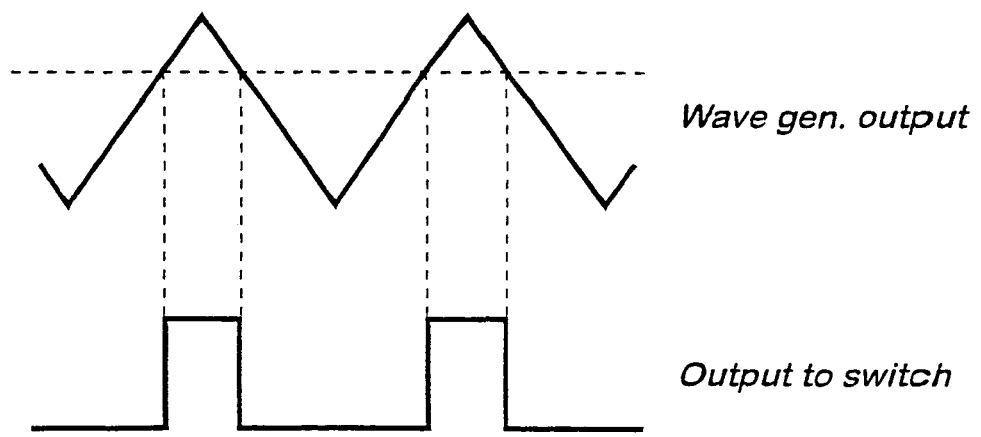

Such adjustment is carried out automatically by the controller 72 using an arrangement in which a signal representative of the load impedance presented to the generator output terminals 62 is applied to a pulse generator having a variable mark-to-space ratio. Referring to FIGS. 8A and 8B in conjunction with FIG. 2, a signal $V_Z$ representative of impedance is generated in the controller 72 by dividing the set output voltage, represented by a signal $V_V$, by the current-representative signal $V_I$ fed to the controller 72 from the current detection circuit 80 (FIG. 2) in a division stage 55 (FIG. 8A). This impedance-dependent signal is compared in a comparator 56 with the output of a triangular wave generator to produce a square wave, as shown in FIG. 8B, that is then supplied to the switching device 51 of FIG. 6 to control the switching between the cut and coag parts of the blended output. In this way, the proportions of the cut and coag signal can be continuously adjusted, depending on the rise and fall of the impedance measured at the surgical site. This produces an electrosurgical apparatus that can react virtually instantaneously to changes in the surgical environment, and in any event much quicker than would be possible should the surgeon or an operating assistant be required to adjust the settings of the generator by the manual pressing of buttons or the use of a foot-pedal or other input mechanism.

Referring back to FIG. 3, the blended signal supplied alternately to the electrodes 2 and 3, or 3 and 40, is not necessarily a blend of cutting and coagulating signals. Both constituent parts of the blended signal could conceivably be cutting RF signals. A cutting signal supplied between electrodes 3 and 40 would produce a much wider RF cut than a cutting signal supplied between electrodes 2 and 3, or 2 and 40. Thus, by varying the amount of the first RF signal (supplied between electrodes 2 and 3) as compared to the second RF signal (supplied between electrodes 3 and 40), the width of the RF cut can be varied in response to the measured parameter.

Similarly, both constituent parts of the blended signal could conceivably be coagulating RF signals. A coagulating signal supplied between electrodes 3 and 40 would produce a much wider RF lesion than a coagulating signal supplied between electrodes 2 and 3, or 2 and 40. Thus, by varying the amount of the first RF signal (supplied between electrodes 2 and 3) as compared to the second RF signal (supplied between electrodes 3 and 40), the width of the RF lesion can be varied in response to the measured parameter.

What is claimed is:

1. An electrosurgical generator for generating radio frequency (RF) power for supply to an electrosurgical instrument, the generator comprising
   (i) at least one source of RF output power,
   (ii) an output stage including at least two output lines adapted to be connected to the electrosurgical instrument,
   (iii) means for measuring a parameter representative of the condition of the tissue encountered during the electrosurgical procedure, and
   (iv) a controller operable to control the generator system such that it is capable of delivering one of a first RF waveform to the output lines and a second RF waveform to the output lines, and, in a combined mode, delivering both first and second RF waveforms, the controller being such that, in the combined mode, the controller automatically adjusts a first proportion of an overall signal being the first RF waveform as compared to a second proportion of the overall signal being the second RF waveform in response to the measured parameter representative of the condition of the tissue during the surgical procedure.

2. An electrosurgical generator according to claim 1, wherein the measured parameter is the impedance measured across two of the output lines.

3. An electrosurgical generator according to claim 1, including first and second sources of radio frequency (RF) power, the first source being connected to deliver the first RF waveform, and the second source being connected to deliver the second RF waveform.

4. An electrosurgical generator according to claim 3, wherein, in the combined mode, the controller is adapted to supply RF waveforms from the first and second sources continuously.

5. An electrosurgical generator according to claim 3, wherein, in the combined mode, the controller is adapted to supply RF waveforms from at least one of the first and second sources discontinuously.

6. An electrosurgical generator according to claim 5, wherein, in the combined mode, the controller is adapted to switch in and out the connection of the first source to deliver the first RF waveform discontinuously.

7. An electrosurgical generator according to claim 5, wherein, in the combined mode, the controller is adapted to switch in and out the connection of the second source to deliver the second RF waveform discontinuously.

8. An electrosurgical generator according to claim 1, including a single source of radio frequency (RF) power, the controller being adapted in the combined mode to alternate between delivering the first RF waveform and the second RF waveform to the output lines as an alternating signal.

9. An electrosurgical generator according to claim 1, wherein the aspect that is adjusted in response to the measured parameter is selected from the power, the voltage and the current of at least one of the first RF waveform and the second RF waveform.

10. An electrosurgical generator according to claim 1, wherein the first RF waveform is a cutting RF waveform designed to produce the electrosurgical cutting of tissue, and the second RF waveform is a coagulating RF waveform designed to produce the electrosurgical coagulation of tissue.

11. An electrosurgical generator according to claim 10, wherein the controller is operable to limit the RF peak output voltage developed across the output connections to at least a first predetermined threshold value for cutting to produce the first cutting RF waveform, and second predetermined threshold value for coagulation to produce the second coagulating RF waveform and, in the combined mode of the generator, to alternate constantly between said first and second threshold values.

12. An electrosurgical generator according to claim 10, wherein the first duty cycle is that part of the overall signal during which the first cutting RF waveform is supplied to the output lines, and the second duty cycle is that part of the overall signal during which the second coagulating RF waveform is supplied to the output lines.

13. An electrosurgical generator according to claim 12, wherein the aspect that is adjusted in response to the measured parameter is at least one of the first and second duty cycles.

14. An electrosurgical generator according to claim 1, including at least three output lines, and also including a selection arrangement for varying the coupling between said at least one source and the three output lines such that, in the combined mode, that part of the combined signal that is the first RF waveform is delivered between a first pair of the output lines, and that part of the combined signal that is the second RF waveform is delivered between a second pair of the output lines.

15. An electrosurgical generator according to claim 14, wherein both the first and second RF waveforms are cutting RF waveforms designed to produce the electrosurgical cutting of tissue.

16. An electrosurgical generator according to claim 14, wherein both the first and second RF waveforms are coagulating RF waveforms designed to produce the electrosurgical coagulation of tissue.

17. An electrosurgical generator according to claim 1, wherein the condition of the tissue is such that the tissue is bleeding.

18. An electrosurgical generator according to claim 1, wherein the condition of the tissue is such that the tissue is dry.

* * * * *